US00PP12854P2

(12) United States Plant Patent
Bergman

(10) Patent No.: US PP12,854 P2
(45) Date of Patent: Aug. 13, 2002

(54) CHRYSANTHEMUM PLANT NAMED 'REGAL YONASHVILLE'

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/774,362

(22) Filed: Feb. 1, 2001

(51) Int. Cl.[7] ..... A01H 5/00

(52) U.S. Cl. ..... Plt./297

(58) Field of Search ..... Plt./297

(56) References Cited

U.S. PATENT DOCUMENTS

PP11,795 P2 * 3/2001 VandenBerg ..... Plt./286

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Regal Yonashville', characterized by its uniform and upright plant habit; strong and vigorous growth habit; dark green foliage; uniform flowering response; early flowering, eight-week response time; very freely flowering habit; large daisy-type inflorescences that are about 7.3 cm in diameter; purple ray florets and bright yellow disc florets; and excellent postproduction longevity with plants maintaining good substance and color for at least four weeks in an interior environment.

1 Drawing Sheet

BACKGROUND OF THE INVENTION

The present Invention relates to a new and distinct cultivar of Chrysanthemum plant, botanically known as *Chrysanthemum×morifolium* and hereinafter referred to by the name 'Regal Yonashville'.

The new Chrysanthemum is a product of a mutation induction program conducted by the Inventor in Fort Myers, Fla. The objective of the program is to create new potted Chrysanthemum cultivars that are suitable for year-round production with uniform plant growth habit, good vigor, desirable inflorescence form and floret colors, fast response time, and excellent postproduction longevity.

The new Chrysanthemum originated by exposing unrooted cuttings of the Chrysanthemum cultivar Yonashville, disclosed in U.S. Plant Pat. No. 11,795, to X-ray radiation in September, 1997 in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Fort Myers, Fla. The new Chrysanthemum was discovered and selected by the Inventor as a single flowering plant within this population in March, 1998, in Fort Myers, Fla. The selection of this plant was based on its uniform plant growth habit, good vigor, desirable inflorescence form and floret colors, fast response time, and excellent postproduction longevity.

Asexual reproduction of the new Chrysanthemum by vegetative tip cuttings was first conducted in Fort Myers, Fla. in June, 1998. Asexual reproduction by cuttings has shown that the unique features of this new Chrysanthemum are stable and reproduced true to type in successive generations.

SUMMARY OF THE INVENTION

The cultivar Regal Yonashville has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Regal Yonashville'. These characteristics in combination distinguish 'Regal Yonashville' as a new and distinct Chrysanthemum:

1. Uniform and upright plant habit.
2. Strong and vigorous growth habit.
3. Dark green foliage.
4. Uniform flowering response.
5. Typically grown as a natural spray-type.
6. Early flowering, eight-week response time.
7. Very freely flowering.
8. Large daisy-type inflorescences that are about 7.3 cm in diameter.
9. Purple ray florets and bright yellow disc florets; ray floret does not fade with development.
10. Excellent postproduction longevity with plants maintaining good substance and color for at least four weeks in an interior environment.

Plants of the new Chrysanthemum can be compared to plants of the cultivar Yonashville. In side-by-side comparisons conducted by the Inventor in Salinas, Calif., plants of the new Chrysanthemum differ from plants of the cultivar Yonashville in the following characteristics:

1. Plants of the new Chrysanthemum flower about one or two days earlier than plants of the cultivar Yonashville.
2. Ray floret color of the new Chrysanthemum is darker than ray floret color of the cultivar Yonashville.

Plants of the new Chrysanthemum can be compared to plants of the Chrysanthemum cultivar Yolompoc, disclosed in U.S. Plant Pat. No. 11,203. In side-by-side comparisons conducted by the Inventor in Salinas, Calif., plants of the new Chrysanthemum differ from plants of the cultivar Yolompoc in the following characteristics:

1. Plants of the new Chrysanthemum are more vigorous and stronger than plants of the cultivar Yolompoc.

2. Plants of the new Chrysanthemum are more freely flowering than plants of the cultivar Yolompoc.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the sheet comprises a top perspective view of a typical flowering plant of 'Regal Yonashville' grown a natural spray-type.

The photograph at the bottom of the sheet comprises a close-up view of typical inflorescences of 'Regal Yonashville' grown as a natural spray-type.

DETAILED BOTANICAL DESCRIPTION

In the following description, color references are made to The Royal Horticultural Society Colour Chart except where general terms of ordinary dictionary significance are used. The following observations and measurements describe plants grown and flowered during the autumn in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 4,000 to 6,000 foot-candles. Four unrooted cuttings were directly stuck in 15-cm containers, exposed to long day/short night conditions, and pinched once about 14 days later. At that time, the photoinductive short day/long night treatments were started. Plants used for this description were grown as natural spray-types. Measurements and numerical values represent averages of typical flowering plants.

Botanical classification: *Chrysanthemum×morifolium* cultivar Regal Yonashville.

Commercial classification: Daisy-type potted Chrysanthemum.

Parentage: Induced mutation of the *Chrysanthemum×morifolium* cultivar Yonashville, disclosed in U.S. Plant Pat. No. 11,795.

Propagation:

*Type*.—Terminal tip cuttings.

*Time to initiate roots*.—About four days at 21° C.

*Time to produce a rooted cutting*.—About ten days at 21° C.

*Root description*.—Fibrous and well-branched.

Plant description:

*Appearance*.—Herbaceous daisy-type potted Chrysanthemum typically grown as a natural spray-type. Stems upright and outwardly spreading; uniform flat crown. Freely branching, about three to four lateral branches develop after removal of terminal apex (pinching); dense and full plants. Vigorous.

*Plant height*.—About 35 cm.

*Plant width*.—About 48 cm.

*Lateral branches*.—Length: About 31 cm. Diameter: About 4 mm. Internode length: About 2.1 cm. Strength: Strong. Texture: Pubescent. Color: 144A.

*Foliage description*.—Arrangement: Alternate. Quantity of leaves per lateral stem: About 15. Length: About 7.3 cm. Width: About 4.7 cm. Apex: Cuspidate to mucronate. Base: Attenuate. Margin: Palmately lobed, sinuses between lateral lobes parallel to divergent. Texture: Upper and lower surfaces with very fine pubescence; veins prominent on lower surface. Color: Young foliage, upper surface: Darker than 147A. Young foliage, lower surface: Darker than 147B. Mature foliage, upper surface: Darker and more green than 147A. Mature foliage, lower surface: Close to 147B. Venation, upper surface: 147A to 147B. Venation, lower surface, 146C. Petiole length: About 1.5 cm. Petiole diameter: About 2 mm. Petiole color: 146C.

Inflorescence description:

*Appearance*.—Daisy-type inflorescence form with elongated oblong-shaped ray florets. Inflorescences borne on terminals above foliage. Disk and ray florets arranged acropetally on a capitulum. Not fragrant. Typically grown as a natural spray-type.

*Flowering response*.—Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about eight weeks later.

*Postproduction longevity*.—Inflorescences maintain good color and substance for at least four weeks in an interior evnironment

*Quantity of inflorescences*.—Very freely flowering, about 14 inflorescences develop per lateral stem, or about 42 to 56 inflorescences per plant.

*Inflorescence bud*.—Height: About 6 mm. Diameter: About 7.5 mm. Color: 143A.

*Inflorescence size*.—Diameter: Large, about 7.3 cm. Depth (height): About 1.8 cm. Diameter of disc: About 1.5 cm. Receptacle diameter: About 6 mm.

*Ray florets*.—Shape: Elongated-oblong. Orientation: Initially upright, then about 60° from vertical. Aspect: Flat, somewhat reflexed. Length: About 3.5 cm. Width: About 1.1 cm. Corolla tube length: About 4 mm. Apex: Mostly acute. Base: Attenuate; short corolla tube. Margin: Entire. Texture: Smooth, glabrous, satiny. Number of ray florets per inflorescence: About 27 arranged in one or two rows. Color: When opening, upper and lower surfaces: 77A. Fully opened, upper surface: 77A; becoming closer to 64A with development. Fully opened, lower surface: 77C to 77D.

*Disc florets*.—Arrangement: Massed at center of receptacle. Shape: Tubular, elongated. Apex: Five-pointed. Length: About 6 mm. Width: Apex, about 1.5 mm; base, about 1 mm. Number of disc florets per inflorescence: About 164. Color: Immature: 154A. Mature: Apex: 9A. Mid-section: 154D. Base: 155D.

*Peduncles*.—Length: First peduncle: About 6 cm. Fourth peduncle: About 7.8 cm. Seventh peduncle: About 10.5 cm. Diameter: About 2.5 mm. Angle to vertical: About 50 to 55° from vertical. Strength: Moderately strong, flexible. Color: 144A.

*Reproductive organs*.—Androecium: Present on disc florets only. Anther color: 9A. Pollen amount: None. Gynoecium: Present on both ray and disc florets. Pistil color: Greenish white.

*Seed*.—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Regal Yonashville', as illustrated and described.

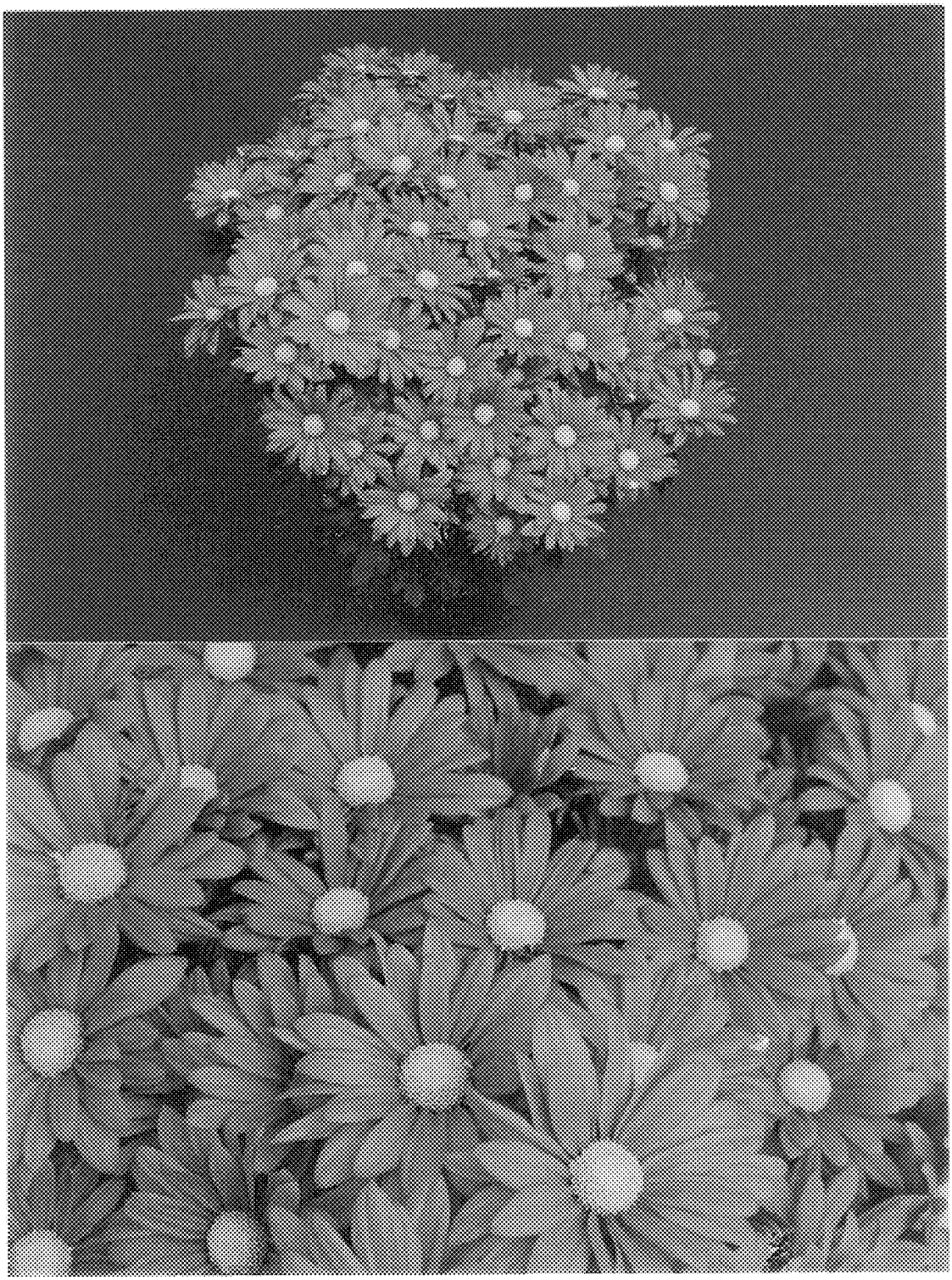

* * * * *